United States Patent
Takase

(10) Patent No.: US 6,730,018 B2
(45) Date of Patent: May 4, 2004

(54) ENDOSCOPE

(75) Inventor: Seisuke Takase, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 09/895,908

(22) Filed: Jun. 29, 2001

(65) Prior Publication Data

US 2002/0004627 A1 Jan. 10, 2002

(30) Foreign Application Priority Data

Jul. 4, 2000 (JP) ........................................ 2000-202544

(51) Int. Cl.$^7$ .............................................. A61B 1/005
(52) U.S. Cl. ........................ 600/139; 600/101; 600/133
(58) Field of Search .............................. 600/130, 139, 600/143, 144, 133

(56) References Cited

U.S. PATENT DOCUMENTS

| | | | |
|---|---|---|---|
| 4,427,000 A | * 1/1984 | Ueda ........................... | 219/201 |
| 4,799,474 A | * 1/1989 | Ueda ........................... | 600/133 |
| 5,058,567 A | * 10/1991 | Takahashi et al. .......... | 600/139 |
| 5,114,402 A | * 5/1992 | McCoy ........................ | 600/143 |
| 5,329,935 A | * 7/1994 | Takahashi ................... | 600/121 |
| 5,345,937 A | * 9/1994 | Middleman et al. ........ | 600/143 |
| 5,482,029 A | * 1/1996 | Sekiguchi et al. .......... | 600/109 |
| 5,577,992 A | * 11/1996 | Chiba et al. ................. | 600/116 |
| 5,645,520 A | * 7/1997 | Nakamura et al. .......... | 600/143 |
| 5,897,488 A | * 4/1999 | Ueda ........................... | 600/143 |
| 5,941,818 A | * 8/1999 | Hori et al. ................... | 600/110 |
| 6,419,628 B1 | * 7/2002 | Rudischhauser et al. .... | 600/161 |

FOREIGN PATENT DOCUMENTS

| | | |
|---|---|---|
| JP | 2-283346 | 11/1990 |
| JP | 6-269397 | 9/1994 |
| JP | 8-136823 | 5/1996 |

\* cited by examiner

*Primary Examiner*—John P. Leubecker
*Assistant Examiner*—Henry M. Johnson, III
(74) *Attorney, Agent, or Firm*—Scully, Scott, Murphy & Presser

(57) ABSTRACT

An endoscope has built-in components, which include a spiral tube, a braid, angulation wires, and angulation coils, passed through a sheathing of a flexible tube that is an integral part of a soft insertion member. Conditions are determined so that the sum total of strengths of forces the built-in components exert in correcting their extent of deformation that is caused by sterilization with high-temperature high-pressure steam will be larger than the strength of force the sheathing exerts in correcting its extent of deformation during the high-temperature high-pressure steam sterilization (which includes a high temperature load). Thus, the extent of deformation derived from sterilization with high-temperature high-pressure steam is suppressed.

7 Claims, 5 Drawing Sheets

ENDOSCOPE

This application claims benefit of Japanese Application No. 2000-202544 filed in Japan on Jul. 4, 2000, the contents of which are incorporated by this reference.

BACKGROUND OF THE INVENTION

1. Field of the Invention

The present invention relates to an endoscope having a soft insertion member and capable of being sterilized with high-temperature high-pressure steam.

2. Description of the Related Art

An endoscope having a soft insertion member is inserted into a tortuous body cavity, whereby endoscopic examination may be carried out or a therapeutic instrument may be, if required, used to perform a cure. Endoscopes are therefore widely used in various fields including the medical field.

For example, Japanese Unexamined Patent Application Publication No. 2-283346 describes an art relating to such an endoscope. Herein, a flexible tube that is an integral part of an insertion member of the endoscope has a two-ply sheathing made of a high polymer material. Consequently, excellent inserting smoothness is ensured and improved durability is offered.

A recent trend is not to use ethylene oxide to sterilize an endoscope from the viewpoint of being friendly to the environment. Therefore, a high-temperature high-pressure steam sterilizer that employs harmless high-temperature high-pressure steam instead of ethylene oxide is sometimes used to sterilize an endoscope.

When such a high-temperature high-pressure steam sterilizer is used to sterilize an endoscope, the endoscope is first stowed in a sterilization case and then sterilized.

However, as mentioned above, when an endoscope is stowed in a sterilization case and then sterilized, the soft insertion member of the endoscope is exposed to high-temperature high-pressure steam while being settled in a tray, which is placed in the case, in a specific shape. A thermal load is applied to the insertion member in the case where tortuousness for a resin used in the insertion member occurs. Consequently, the insertion member may be deformed in the specific shape, which is defined by the tray, at the room temperature after completion of sterilization. This may affect inserting smoothness and maneuverability.

SUMMARY OF THE INVENTION

Accordingly, an object of the present invention is to provide an endoscope that is bent by a small magnitude at room temperature after completion of sterilization with high-temperature high-pressure steam. The endoscope can therefore offer improved inserting smoothness and maneuverability.

Briefly, according to the present invention, there is provided an endoscope having a soft insertion member. The insertion member consists mainly of a flexible tube whose sheathing layer is made of a resin and one or more built-in components incorporated in the flexible tube. At least one of the built-in components deforms by an extent smaller than an extent by which the flexible tube deforms, at room temperature, after being subjected to a high-temperature high-pressure steam sterilization (which includes a high temperature load) that is performed with the insertion member settled in a specific shape.

The above and other objects, features and advantages of the invention will become more apparent from the following description when taken in conjunction with the accompanying drawings.

DESCRIPTION OF THE PREFERRED EMBODIMENTS

Figure 1:
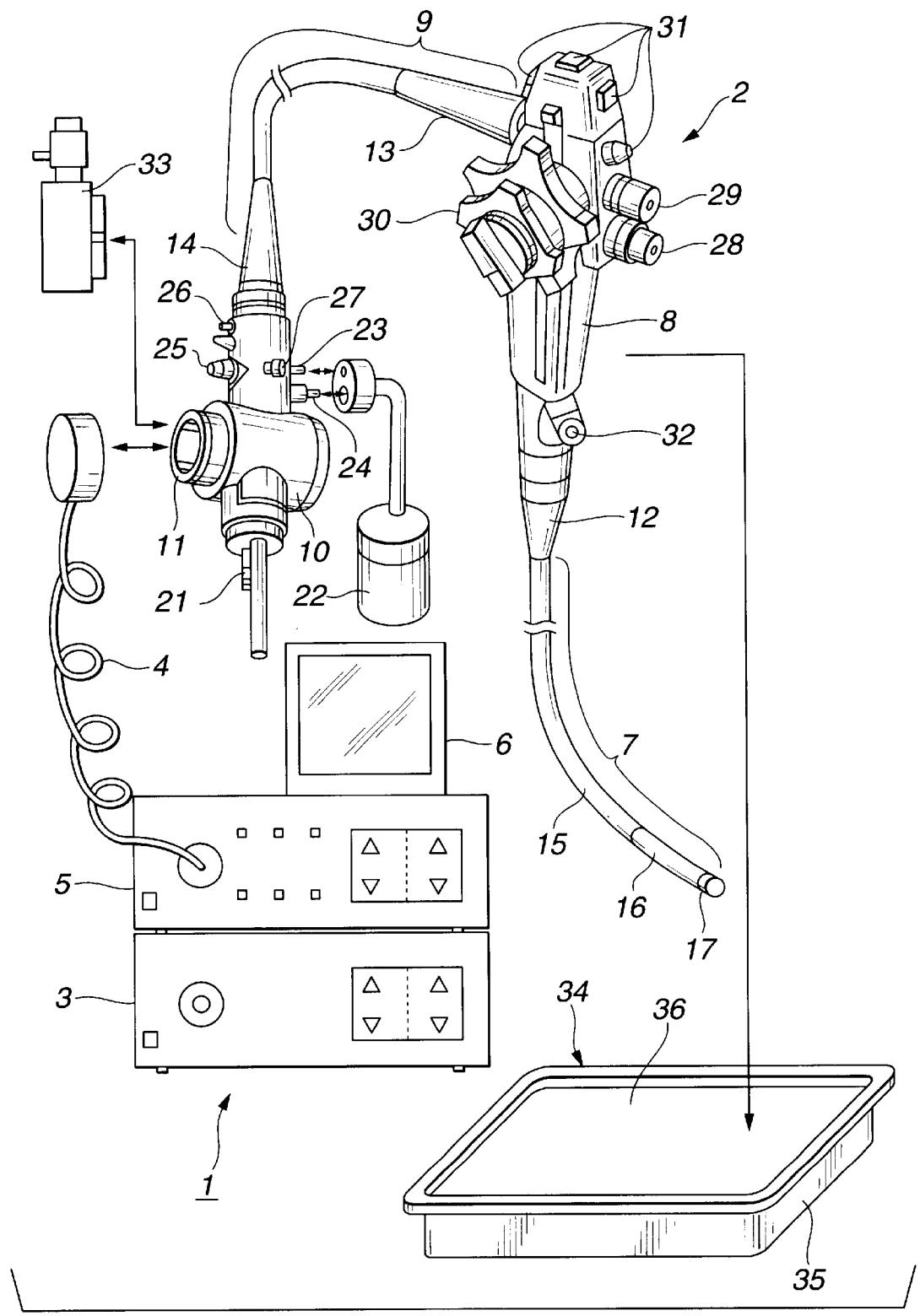
FIG. 1 is a perspective view showing the overall configuration of an endoscope system employed in a first embodiment of the present invention.

Referring to the drawings, embodiments of the present invention will be described below.

First Embodiment

Figure 2:
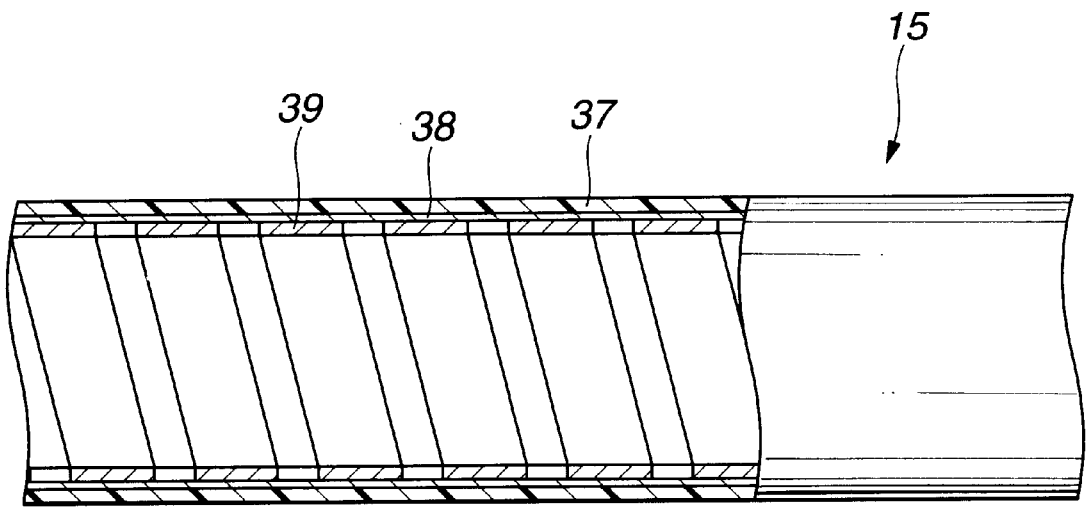
FIG. 2 is a partially sectional view showing the tubular structure of a flexible tube employed in the first embodiment.
Figure 3:
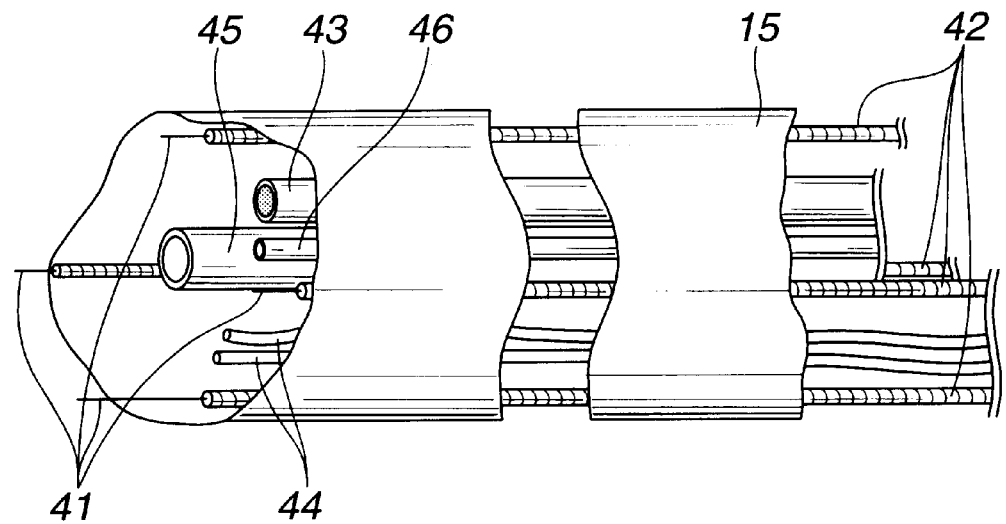
FIG. 3 shows built-in components incorporated in the flexible tube employed in the first embodiment.
Figure 4:
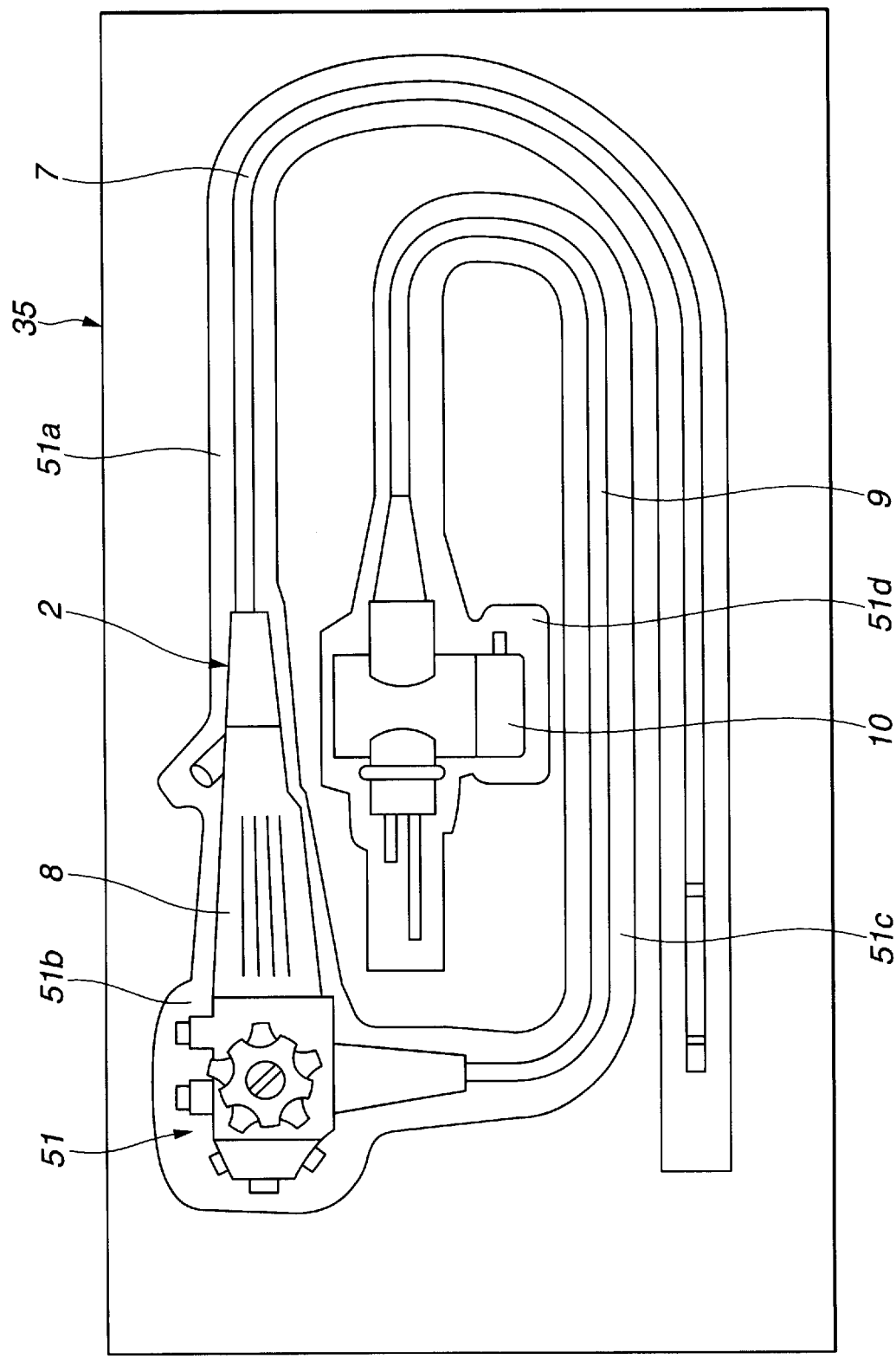
FIG. 4 shows an endoscope in accordance with the first embodiment stowed in a tray.
Figure 5A:
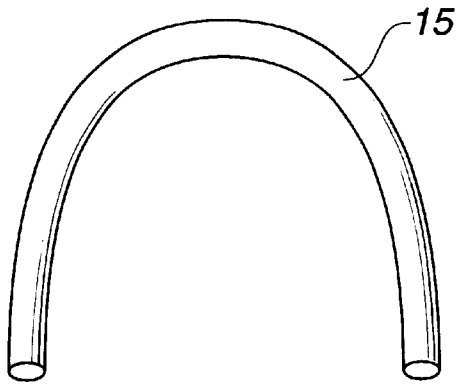
FIG. 5A, FIG. 5B, and FIG. 5C are conceptual diagrams showing degrees of bend by which a flexible tube, a built-in component, and an insertion member that are employed in the first embodiment are bent after completion of sterilization with high-temperature high-pressure steam.
Figure 5B:
Figure 5C:
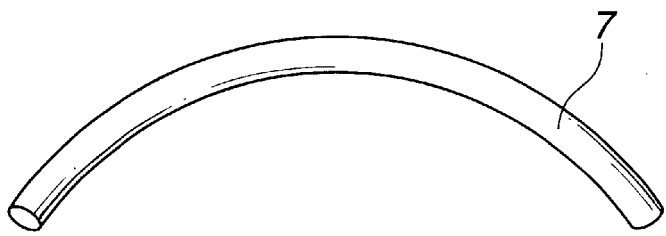

FIG. 1 to FIG. 5C are concerned with a first embodiment of the present invention. FIG. 1 shows the overall configuration of an endoscope system employed in the first embodiment. FIG. 2 shows the tubular structure of a flexible tube. FIG. 3 shows built-in components incorporated in the flexible tube. FIG. 4 shows an endoscope stowed in a tray. FIG. 5A, FIG. 5B, and FIG. 5C conceptually show degrees of bend by which the flexible tube, a built-in component, and an insertion member are bent after completion of sterilization with high-temperature high-pressure steam.

As shown in FIG. 1, an endoscope system 1 comprises an endoscope 2, a light source apparatus 3, a video processor 5, and a monitor 6. The endoscope 2 has an imaging means and a light guide. The light source apparatus 3 supplies illumination light to the light guide and is freely connected to or from the endoscope 2 so that the light source apparatus 3 can be freely disconnected therefrom. The video processor 5 is connected to the endoscope 2 over a signal cable 4, controls the imaging means incorporated in the endoscope 2, and processes a signal generated by the imaging means. A picture depicting an object and being outputted from the video processor 5 is displayed on the monitor 6.

The endoscope 2 is structured to be able to be cleaned after used for the purpose of observation or treatment, and to be able to be sterilized with high-temperature high-pressure steam after it is cleaned.

The endoscope 2 includes an elongated insertion member 7, a control section 8, a linkage cord 9, a connector unit 10, and an electric connector 11. The insertion member 7 is flexible (soft). The control section 8 is coupled to the proximal end of the insertion member 7. The linkage cord 9 that is flexible is extended from the lateral part of the control section 8. The connector unit 10 is fixed to one end of the linkage cord 9, and joined to the light source apparatus 3 so that it can be disjoined freely. The electric connector 11 is formed as a lateral part of the connector unit 10.

A connector fixed to one end of the signal cable 4 is mated with the electric connector 11 so that the connector can be separated freely. The signal cable 4 is coupled to the video processor 5. A pressure regulating valve-inclusive waterproof cap 33 can be freely detachably attached to the electric connector 11. The pressure regulating valve-inclusive waterproof cap 33 has a pressure regulating valve (not shown). The electric connector 11 has an air vent hole (not shown), and the vent of the air vent hole opens onto outside. The air vent hole links the interior and exterior of the endoscope 2.

The insertion member 7 has an anti-insertion member breakage member 12, which is made of an elastic material, fixed to the proximal end thereof. The anti-insertion member breakage member 12 prevents abrupt bend of a joint that is joined to the control section 8.

Moreover, an anti-control section breakage member 13 having the same ability as the anti-insertion member breakage member 12 is included as a joint linking the control section 8 and linkage cord 9. An anti-connector breakage member 14 having the same ability as the anti-insertion member breakage member 12 is included as a joint linking the linkage cord 9 and connector unit 10.

The insertion member 7 comprises a flexible tube 15, a bending section 16, and a distal part 17. The flexible tube 15 is flexible and soft. The bending section 16 is fixed to the distal end of the flexible tube 15 and can be bent remotely using the control section 8. The distal part 17 is fixed to the distal end of the bending section 16. An observation optical system and an illumination optical system (not shown) are incorporated in the distal part 17.

An aeration/perfusion nozzle, a suction port, and a fluid supply port are bored in the distal part 17. When a manipulation is made in order to aerate or perfuse the endoscope, cleaning fluid or gas is jet out to an optical member located on the outer surface of the observation optical system through the aeration/perfusion nozzle. The suction port is an opening bored in the distal end of a therapeutic instrument passage channel run through the insertion member 7. Fluid is jetted out to an object to be observed through the fluid supply port. The therapeutic instrument passage channel is used to pass a therapeutic instrument into a body cavity or suck fluid therefrom.

The connector unit 10 has an air supply base 21, a water supply tank pressurization base 23, and a fluid supply base 24. The air supply base 21 is connected to an air source (not shown) incorporated in the light source apparatus 3 so that the air supply base 21 can be disconnected freely. The water supply tank pressurization base 23 is connected to a water supply tank 22 that is a fluid source so that the water supply tank pressurization base 23 can be disconnected freely.

Moreover, the connector unit 10 has a suction base 25 and an injection base 26. The suction base 25 is connected to a sucking device (not shown) used to suck fluid through the suction port. The injection base 26 is connected to a water supply means (not shown) used to supply water through the fluid supply port.

Furthermore, the connector unit 10 has a ground base 27. When diathermy or the like is carried out, there is a possibility that high-frequency leakage current may flow into the endoscope 2. The ground base 27 is used to feed the developed leakage current from the endoscope 2 back to a diathermy device.

The control section 8 has an aeration/perfusion button 28, a suction button 29, an angulation knob 30, a plurality of remote control switches 31, and a therapeutic instrument insertion port 32. The aeration/perfusion button 28 is pressed in order to instruct aeration or perfusion. The suction button 29 is pressed in order to suck fluid. The angulation knob 30 is manipulated in order to bend the bending section 16. The plurality of remote-control switches 31 is used to remotely control the video processor 5. The therapeutic instrument insertion port 32 is an opening that opens onto the therapeutic instrument passage channel.

Moreover, when the endoscope 2 is sterilized with high-temperature high-pressure steam, a sterilization case 34 is used to stow the endoscope 2.

The sterilization case 34 comprises a tray 35 whose upper side is left open, and a lid member 36 with which the opening of the tray 35 is covered.

The tray 35 and lid member 36 each have a plurality of pores (not shown). When the endoscope is sterilized with high-temperature high-pressure steam using a high-temperature high-pressure steam sterilizer, the high-temperature high-pressure steam permeates the endoscope through the pores.

The tray 35 has a stowage dent 51 (see FIG. 4) formed in conformity to the shape of the endoscope 2 so that the parts of the endoscope 2 will be settled at predetermined positions. For example, the elongated insertion member 7 that is flexible is stowed in a concave insertion-member part 51 a formed as an integral part of the stowage dent 51.

As for typical conditions for sterilization using high-temperature high-pressure steam, the temperature and time for sterilization are described in, for example, the standard ANSI/AAMI ST37-1992 recommended by the American National Standards Institute (ANSI) and published by the Association for the Advancement of Medical Instrumentation (AAMI). Namely, the standard stipulates that a pre-vacuum process should be performed at 132° for four minutes, and that a gravity settling process should be performed at 132° for ten minutes.

The temperature for high-temperature high-pressure steam sterilization (which includes a high temperature load) varies depending on the model of a high-temperature high-pressure sterilizer or the time for a sterilization process. However, generally, the temperature ranges from about 115° C. to about 138° C. (for example, substantially 140° C.). However, some types of sterilizers can be set to about 142° C.

Moreover, the time for sterilization using high-temperature high-pressure steam varies depending on the temperature used for sterilization. Generally, the time ranges from about 3 min to about 60 min. However, some types of sterilizers can be set to about 100 min.

The pressure in a sterilization chamber is, generally, set to a value that is greater than the atmospheric pressure by 0.2 MPa.

According to a typical pre-vacuum high-temperature high-pressure steam sterilization process, a pre-vacuum step is succeeded by a sterilization step at which high-temperature high-pressure steam is fed into the sterilization chamber for the purpose of sterilization.

The pre-vacuum step succeeded by the sterilization step is a step of sucking air from the sterilization chamber, in which equipment to be sterilized is stowed, so as to decompress the sterilization chamber prior to sterilization. The inclusion of the pre-vacuum step enables steam to permeate into the details of the equipment to be sterilized at the succeeding sterilization step.

At the pre-vacuum step, the pressure in the sterilization chamber is set to a value that is smaller than the atmospheric pressure by a value ranging from about 0.07 MPa to about 0.09 MPa.

In some sterilizers, the sterilization step is succeeded by a dry step at which the sterilization chamber is decompressed again in order to dry the sterilized equipment to be sterilized. At the dry step, the sterilization chamber is decompressed in order to exhaust steam from the sterilization chamber in order to facilitate drying of the equipment to be sterilized placed in the sterilization chamber.

At the dry step, the pressure in the sterilization chamber is set to a value that is smaller than the atmospheric pressure by a value ranging from about 0.07 MPa to about 0.09 MPa.

When the endoscope 2 is sterilized with high-temperature high-pressure steam, the pressure regulating valve-inclusive waterproof cap 33 is attached to the electric connector 11. At this time, the pressure regulating valve (not shown) of the pressure regulating valve-inclusive waterproof cap 33 is closed, and the vent is blocked with the pressure regulating valve-inclusive waterproof cap 33. Thus, the interior of the endoscope 2 is sealed from outside and kept watertight.

When a sterilization process including the pre-vacuum step is adopted, the pressure in the sterilization chamber is decreased at the pre-vacuum step. Consequently, the external pressure of the endoscope 2 gets lower than the internal pressure thereof. Consequently, the pressure regulating valve is opened due to the difference in pressure. Eventually, the interior of the endoscope 2 communicates with the exterior thereof through the vent for fear a large difference in pressure may be created between the interior of the endoscope 2 and the sterilization chamber. This mechanism protects the endoscope 2 from being damaged because of the difference in pressure between the interior thereof and the exterior thereof.

At the sterilization step, the sterilization chamber is pressurized. When the external pressure of the endoscope 2 gets higher than the internal pressure thereof, the pressure regulating valve is closed due to the difference in pressure. Thus, the high-temperature high-pressure steam will not actively invade into the endoscope 2 through the pressure regulating valve-inclusive waterproof cap 33 and the vent.

However, the high-temperature high-pressure steam gradually invades through a sheathing 37 of the flexible tube 15 (see FIG. 2) or O rings. The sheathing 37 is a sheathing layer made of a high-polymer resin. The O rings made of a fluorocarbon rubber or silicon rubber serve as sealing means and are included in joints of parts of the housing of the endoscope 2. The interior of the endoscope is therefore sterilized reliably.

Pressure that is the sum of pressure released during decompression performed at the pre-vacuum step and pressure added at the sterilization step is applied externally to the housing of the endoscope 2.

Furthermore, when a sterilization process having the decompression step preceded by the sterilization step is adopted, the pressure in the sterilization chamber is lowered at the decompression step. Consequently, the external pressure of the endoscope 2 gets lower than the internal pressure thereof. Due to the difference in pressure, the pressure regulating valve is opened nearly simultaneously with occurrence of the difference in pressure. The interior of the endoscope 2 communicates with the exterior thereof through the vent, whereby a large difference in pressure is prevented from occurring between the interior of the endoscope 2 and the sterilization chamber. Thus, the endoscope 2 is protected from being damaged due to the difference in pressure between the interior and exterior of the endoscope.

After the sterilization step is completed, the sterilization chamber is pressurized. When the external pressure of the endoscope 2 gets higher than the internal pressure thereof, the pressure regulating valve is closed due to the difference in pressure.

When all the steps of high-temperature high-pressure steam sterilization are completed, pressure equivalent to pressure released at the last decompression step is externally applied to the housing of the endoscope 2.

In this state, if the pressure regulating valve-inclusive waterproof cap 33 is detached from the electric connector 11, the interior of the endoscope 2 communicates with the exterior thereof through the vent. The internal pressure of the endoscope 2 becomes equal to the atmospheric pressure. Consequently, the housing of the endoscope 2 is released from a load stemming from the pressure applied thereto.

FIG. 2 shows the tubular structure of the flexible tube 15.

In the flexible tube 15, there are provided, as built-in components, a braid 38 which is a metal woven like a net, a spiral tube 39 which is made by spirally winding a metallic belt and covered with the braid 38 at the inner side of the sheathing 37 made of a resin. The spiral tube 39, the braid 38 and the sheathing 37 constitute a three-ply flexible tube.

The resin made into the sheathing 37 is, for example, an ester-series thermoplastic elastomer but not limited to it. Alternatively, any other resin, for example, an amide-series thermoplastic elastomer, a styrene resin, a fluorocarbon rubber, or a silicon rubber will do.

These resins that may be adopted to make the sheathing 37 are selected in consideration of the durability of an endoscope used by a user, the inserting smoothness thereof, or the like, or in consideration of chemical resistance against an agent used to clean or disinfect an endoscope. Many resins are thermally deformed at a temperature lower than the temperature used for high-temperature high-pressure steam sterilization (which includes a high temperature load).

FIG. 3 shows the built-in components incorporated in the flexible tube 15.

The built-in components incorporated in the flexible tube 15, or more particularly, in the built-in component spiral tube 39, include angulation wires 41 and angulation coils 42, a light guide 43, signal cables 44, a therapeutic instrument passage channel 45, and an aeration/perfusion tube 46. The angulation wires 41 and angulation coils 42 are used to remotely control the bending section 16. Illumination light is propagated over the light guide 43. These components are elongated and passed through the spiral tube 39.

The built-in components are made of materials that are deformed at a temperature higher than the temperature for high-temperature high-pressure steam sterilization (loading step).

Incidentally, in the present specification, the temperature of thermal deformation at which a component is thermally deformed shall be defined as the temperature at which the component of the endoscope 2 starts deforming when thermally loaded at high temperature. The temperature of thermal deformation is therefore different from the critical temperature above which the endoscope 2 fails to exert its original capability.

Moreover, the spiral tube 39, braid 38, angulation wires (angle control wires) 41, angulation coils (angle control coils) 42, light guide 43, signal cables 44, therapeutic instrument passage channel 45, and aeration/perfusion tube 46 that are the built-in components of the sheathing 37 of the flexible tube 15 each exert force in correcting its deformation that is derived from high-temperature high-pressure steam sterilization. The strength of the force exerted by the spiral tube 39 shall be H1, the strength of the force exerted by the braid 38 shall be H2, and the strength of the force exerted by the angulation wires 41 shall be H3. Moreover, the strength of the force exerted by the angulation coils 42 shall be H4, the strength of the force exerted by the light guide 43 shall be H5, and the strength of the force exerted by the signal cables 44 shall be H6. Moreover, the strength of the force exerted by the therapeutic instrument passage channel 45 shall be H7, and the strength of the force exerted by the aeration/perfusion tube 46 shall be H8. The sum total of the strengths of the forces exerted in correcting deformation shall be Hn (that is, Hn=H1+H2+H3+H4+H5+H6+H7+H8). The strength of force the sheathing 37 exerts in deforming during high-temperature high-pressure steam sterilization (strength of force exerted in maintaining a bent state) shall be Hj. In this case, the conditions are determined so that the relationship of Hn>Hj will be established.

What is referred to as the strength of force exerted in correcting deformation is the strength of force exerted in keeping straight against force, which is exerted in deforming when heated during high-temperature high-pressure steam sterilization, before or after the sterilization.

To be more specific, at least one of built-in components deforms by an extent smaller than the extent by which the sheathing 37 deforms, during sterilization with high-temperature high-pressure steam. Therefore, when the built-in components are incorporated in the insertion member 7, Hn is larger than Hj.

FIG. 4 shows the endoscope 2 stowed in the tray 35 that is used to sterilize the endoscope 2 using a high-temperature high-pressure steam sterilizer.

As described above, the tray 35 has the stowage dent 51 composed of the concave parts that are contoured to fit the parts of the endoscope 2. The parts of the endoscope 2 are settled in the predetermined concave parts of the stowage dent 51.

For example, the insertion member 7 is stowed in the concave insertion-member part 51a, the control section 8 is stowed in the concave control-section part 51b, the linkage cord 9 is stowed in the concave linkage-cord part 51c, and the connector unit 10 is stowed in the concave connector-unit part 51d.

After the endoscope 2 is stowed in the tray 35 as shown in FIG. 4, the tray 35 is covered with the lid member 36. Thereafter, a high-temperature high-pressure steam sterilizer is used to sterilize the endoscope 2.

FIG. 5A, FIG. 5B, and FIG. 5C conceptually show the degrees of bend by which the flexible tube 15, the built-in component 55 of the flexible tube 15, and the insertion member 7 are bent at room temperature when taken out of the tray 35 after completion of high-temperature high-pressure steam sterilization (which includes a high temperature load).

After the flexible tube 15 alone and the endoscope 2 are sterilized with high-temperature high-pressure steam, the degrees of bend by which they are bent before the sterilization are compared with the degrees of bend by which they are bent after the sterilization. Thus, an extent of deformation by which the built-in components are bent and an extent of deformation by which the flexible tube 15 is bent can be checked.

Next, operations to be exerted by the present embodiment will be described below.

When the endoscope 2 is sterilized using a high-temperature high-pressure steam sterilizer, the endoscope is stowed in the tray 35. The insertion member 7 is therefore loaded during high-temperature high-pressure steam sterilization while being fitted in the concave insertion-member part 51a of the tray 35. At this time, the sheathing 37 of the flexible tube 15 changes its states to enter a state in which the sheathing 37 can exert the force Hj in deforming in conformity to the bent state of the endoscope 2.

However, at least one of the built-in components is formed with a member that deforms by a small extent of thermal deformation. The built-in components therefore exert force in keeping straight. At this time, the strength Hn of force exerted in preventing deformation and correcting a deformed state has, as mentioned above, the relationship of Hn>Hj. Even when the sheathing 37 is deformed to bend, the extent of deformation is suppressed. In other words, an extent of deformation by which the insertion member 7 (the flexible tube 15 having the built-in components incorporated) is bent is smaller than an extent of deformation by which the sole flexible tube 15 that does not contain the built-in components is bent.

The temperature of thermal deformation at which the built-in components deform is higher than the temperature resulting from a thermal load imposed during sterilization with high-temperature high-pressure steam. The presence of the built-in components therefore controls the deformation of the sheathing 37 to some extent.

As shown in FIG. 5A, after sterilization with high-temperature high-pressure steam is completed, the flexible tube 15 alone is bent by a larger extent of deformation.

As shown in FIG. 5B, after sterilization with high-temperature high-pressure steam is completed, the built-in components 55 are bent by only a small extent of deformation as a whole. This is because at least one of the built-in components 55 is a member that thermally deforms by a small extent of thermal deformation. Incidentally, the built-in components 55 include the spiral tube 39, braid 38, angulation wires 41, angulation coils 42, light guide 43, signal cables 44, therapeutic accessory passage channel 45, and aeration/perfusion tube 46.

Furthermore, an extent of deformation by which the flexible tube having all the built-in components incorporated therein is bent is smaller than the extent of deformation by which the flexible tube 15 alone is bent.

As shown in FIG. 5C, the insertion member 7 composed of the flexible tube 15 and built-in components 55 is bent by a smaller extent of deformation than the extent of deformation by which the flexible tube 15 alone is bent. This is apparent from the extents of deformation shown in FIG. 5A and FIG. 5B and the relationship of Hn>Hj.

The foregoing first embodiment provides advantages described below.

The extent of deformation by which the built-in components 55 are bent after completion of sterilization with high-temperature high-pressure steam is smaller than the extent of deformation by which the sheathing 37 is bent. Therefore, the extent of deformation by which the insertion member 7 of the endoscope 2 is bent is minimized. Consequently, the deformation of the insertion member 7 is suppressed. This results in excellent inserting smoothness and maneuverability.

Second Embodiment

Next, a second embodiment of the present invention will be described with reference to FIG. 6. The description of the components of the second embodiment identical to those of the first embodiment will be omitted, and different points will be described mainly.

Figure 6:
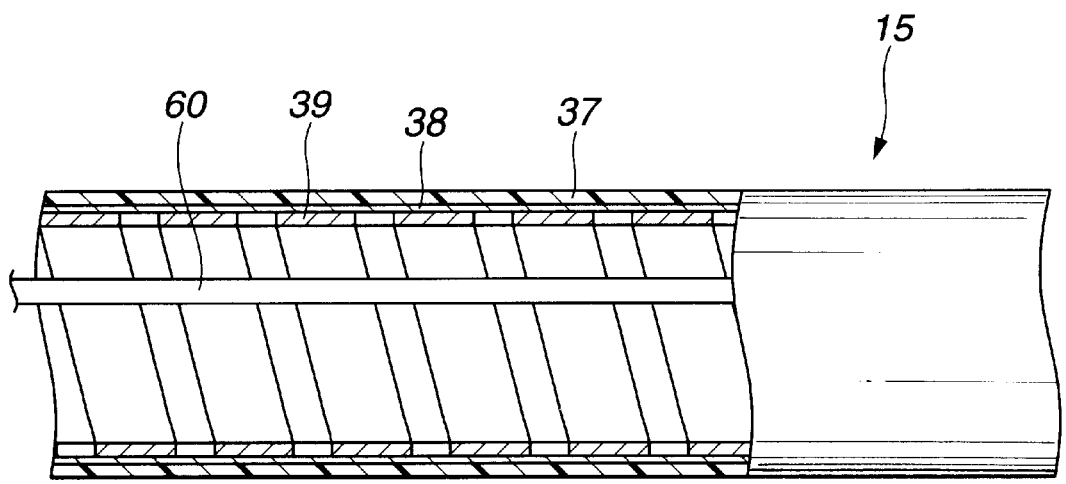
FIG. 6 is a sectional diagram showing the structure of a flexible tube, through which a wire runs, employed in a second embodiment of the present invention.

FIG. 6 shows a structure having a wire 60 run through the flexible tube 15.

The structure of the flexible tube 15 itself is identical to the one shown in FIG. 2.

The wire 60 made of a metal is, as shown in FIG. 6, passed through the flexible tube 15. The metal made into the wire 60 is, for example, a super-elastic alloy or a stainless steel such as SUS304.

The wire 60 is fixed to the inner wall of the flexible tube 15 and to the ends in longitudinal directions of the flexible tube 15, though the fixation is not shown. Incidentally, the wire 60 may be locked in the insertion member 7 or fixed to the end of the control section 8. Furthermore, when it comes to a structure having the wire 60 secured, either a structure having both the ends of the wire 60 secured or a structure having one of the ends secured will do.

The other components are identical to those of the first embodiment.

Next, operations to be exerted by the present embodiment will be described below.

The wire 60 that is an elongated metallic member is incorporated in the flexible tube 15. Therefore, the strength of force exerted in suppressing deformation of bend of the built-in components of the insertion member 7 which is derived from a thermal load imposed during high-temperature high-pressure steam sterilization is greater than that exerted in the first embodiment.

The second embodiment can reliably provide almost the same advantages as the first embodiment.

Third Embodiment

Next, a third embodiment of the present invention will be described with reference to FIG. 7. The description of components of the third embodiment identical to those of the first and second embodiment will be omitted, and different points alone will be described mainly.

Figure 7:
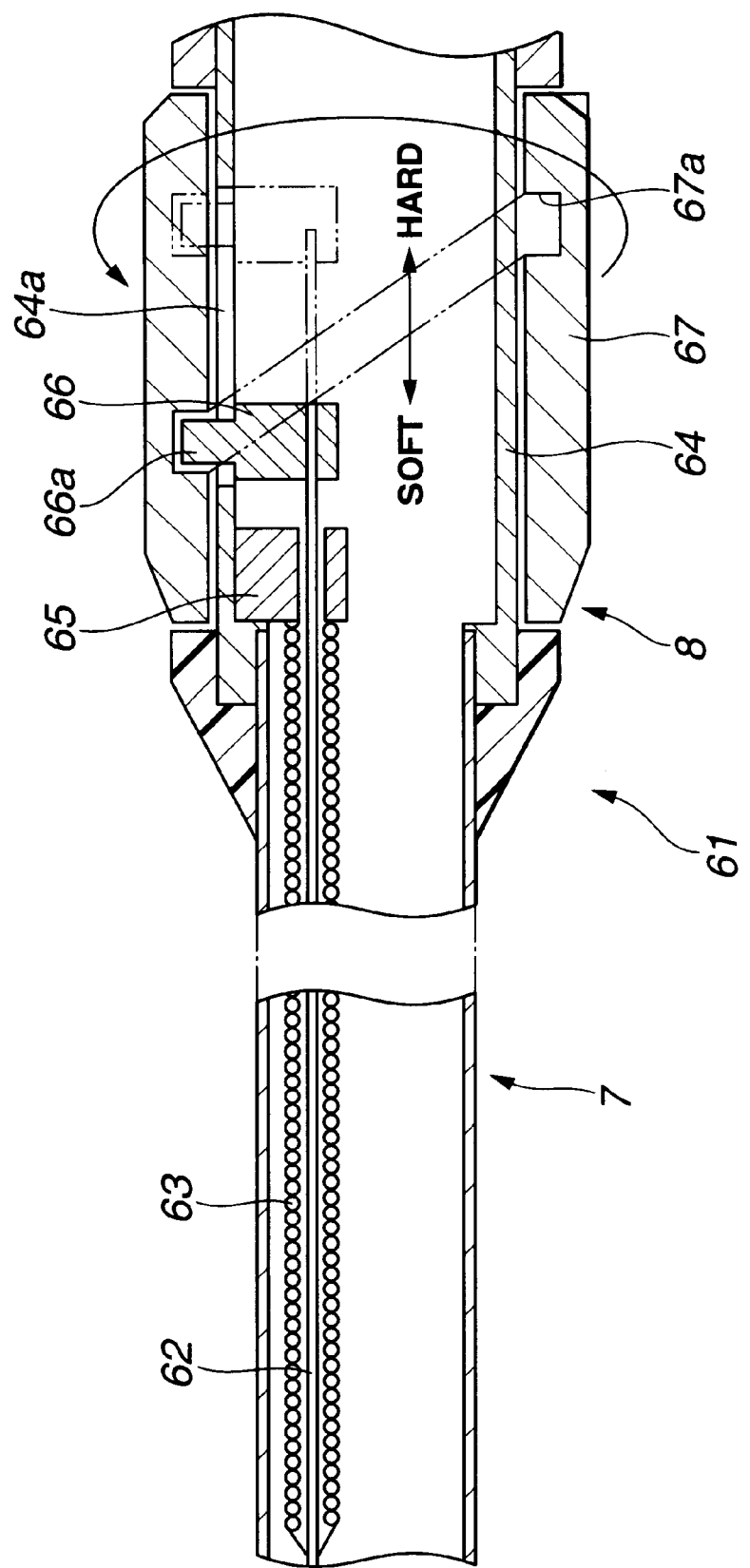
FIG. 7 is a sectional view showing the structures of an insertion member and a control section of an endoscope in accordance with a third embodiment of the present invention.

FIG. 7 shows a structure extending from the end of the control section 8 to the insertion member 7.

According to the present embodiment, as described below, an endoscope 61 is structured so that the flexibility (rigidity) of the flexible tube 15 can be varied or adjusted. By raising the rigidity, the insertion member 7 can be straightened. Therefore, the endoscope 61 of the present embodiment can be said to include a means for changing the flexibility or rigidity of the flexible tube 15.

An adjustment wire 62 and an adjustment coil 63 are incorporated in the flexible tube 15. The adjustment wire 62 is used to trigger a movement needed to adjust the flexibility (rigidity) of the flexible tube 15. The adjustment coil 63 through which the adjustment wire 62 lies is required in order to adjust the flexibility of the flexible tube 15.

The distal part of the adjustment wire 62 is fixed to, for example, the distal part of the insertion member 7.

Moreover, the distal part of the adjustment coil 63 is fixed to the distal end of the adjustment wire 62 by performing brazing or the like.

Furthermore, the backward movement of the rear end of the adjustment coil 63 is restricted by a coil stopper 65 whose outer edge is fixed to a cylindrical body 64 of the control section 8.

The rear end of the adjustment wire 62 lying through the adjustment coil 63 is passed through a hole bored in the coil stopper 65 and fixed to a traction member 66. The traction member 66 is located behind the coil stopper 63 and movable back and forth.

The traction member 66 has a pin 66a jutted outwards. The pin 66a penetrates through an oblong hole 64a that is shaped to be oblong back and forth and formed in the cylindrical body 64, and engages with a cam groove 67a formed in the inner surface of an adjustment knob 67.

The adjustment knob 67 is a cylindrical member that is mounted on the cylindrical body 64 and freely rotatable.

When the adjustment knob 67 is turned in the direction of an arrow, the traction member 66 moves backwards. This causes the rear end of the adjustment wire 62 to move backwards.

Moreover, when the adjustment knob 67 is turned in a direction opposite to the direction of the arrow, the traction member 66 moves forwards. This causes the rear end of the adjustment wire 62 to move forwards.

Owing to the foregoing structure, when the rear end of the adjustment wire 62 is located at the foremost position, almost no compressive force is applied to the adjustment coil 63. The flexible tube 15 exhibits the highest flexibility (the flexible tube is soft).

As the rear end of the adjustment wire 62 moves backwards from the foremost position, compressive force applied to the adjustment coil 63 gets greater. Thus, the rigidity of the flexible tube 15 containing the adjustment coil 63 is maximized.

Next, operations to be exerted by the present embodiment will be described below.

When the adjustment knob 67 is turned in the direction of the arrow, the proximal end of the adjustment wire 62 is pulled together with the traction member 66 owing to the cam mechanism. Consequently, compressive force is applied to the adjustment coil 63. Eventually, the rigidity of the adjustment coil 63 itself gets higher.

Consequently, correction force is produced to restore the insertion member 7, which is held bent at the room temperature after completion of sterilization with high-temperature high-pressure steam, to an almost straight state. The extent of deformation by which the insertion member 7 is bent is thus reduced.

The foregoing third embodiment provides almost the same advantages as the first and second embodiments. In addition, since a flexibility changing means formed with a rigid adjusting means is incorporated, the bent shape of the insertion member 7 is corrected in order to straighten the insertion member 7. This results in excellent inserting smoothness and maneuverability.

Having described the preferred embodiments of the invention referring to the accompanying drawings, it is to be understood that the invention is not limited to those precise embodiments and that various changes and modifications thereof could be effected by one skilled in the art without departing from the spirit or scope of the invention as defined in the appended claims.

What is claimed is:

1. An endoscope comprising:
   a soft insertion member that includes a flexible tube, the insertion member having a sheathing layer;
   a spiral tube, a braid, angulation wires, angulation coils, a light guide, signal cables, a therapeutic instrument passage channel and an aeration/perfusion tube provided at an inner side of the sheathing layer as built-in components; and an elongated metallic member provided as another built-in component, wherein the elongated metallic member suppresses deformation of the insertion member that is derived from a high-temperature load imposed during high-temperature high-pressure steam sterilization.

2. An endoscope according to claim 1, wherein a temperature of thermal deformation at which the elongated metallic member deforms is higher than a temperature of the high-temperature load, and a temperature of thermal deformation at which the sheathing layer deforms is lower than the temperature of the high-temperature load.

3. An endoscope according to claim 1, wherein the elongated metallic member is made of a super-elastic alloy.

4. An endoscope according to claim 1, wherein the elongated metallic member is made of a stainless steel.

5. An endoscope according to claim 1, wherein the sheathing layer is made of a resin.

6. An endoscope according to claim 1, wherein the high-temperature load is achieved at a temperature that ranges from substantially 115° C. to substantially 142° C.

7. An endoscope according to claim 1, further comprising means for changing the flexibility of the flexible tube.

* * * * *